United States Patent [19]
Diamond et al.

[11] 4,117,165
[45] Sep. 26, 1978

[54] AMIDINOUREAS

[75] Inventors: Julius Diamond, Morris Plains, N.J.; Jerome J. Zalipsky, Melrose Park, Pa.

[73] Assignee: William H. Rorer, Inc., Fort Washington, Pa.

[21] Appl. No.: 628,857

[22] Filed: Nov. 5, 1975

Related U.S. Application Data

[63] Continuation-in-part of Ser. No. 379,627, Jul. 16, 1973, abandoned.

[51] Int. Cl.$^2$ .................... A61K 31/17; C07C 127/19
[52] U.S. Cl. ........................... 424/322; 260/553 A
[58] Field of Search .................... 424/322; 260/553 A

[56] References Cited

U.S. PATENT DOCUMENTS 3,539,616  11/1970  Walls .................... 260/553 A

FOREIGN PATENT DOCUMENTS 2,047,879  3/1971  France .................... 260/553 A
2,132,028  1/1972  Fed. Rep. of Germany ...... 260/553 A

OTHER PUBLICATIONS

Skowronska-Serafin et al. –*Tetrahedron* vol. 10, pp. 12–25, (1960).

*Primary Examiner*—Frederick E. Waddell
*Attorney, Agent, or Firm*—James A. Nicholson; John C. Smith, Jr.

[57] ABSTRACT

This invention describes novel chemical compounds which are 1-amidino-3-phenylureas. The method of preparing these compounds and their pharmaceutical uses is also disclosed.

58 Claims, No Drawings

AMIDINOUREAS

This is a continuation-in-part application of our copending U.S. Ser. No. 379,627 filed July 16, 1973, now abandoned.

DESCRIPTION OF PREFERRED EMBODIMENTS

This invention describes a class of novel chemical compounds which comprises a urea moiety which is substituted in the 1-position by an amidino group and in the 3-position with a substituted phenyl ring thus forming 1-amidino-3-substitutedphenylureas. This invention also describes the non-toxic pharmaceutically acceptable salts; the method of preparing these compounds; and their pharmaceutical uses.

The novel compounds of this invention are described by the structural formula I

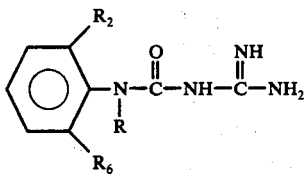

where:
R is hydrogen or loweralkyl;
$R_2$ is loweralkyl;
$R_6$ is halo, loweralkoxy, loweralkyl, haloloweralkyl, nitro or loweralkylsulfonyl; and the non-toxic acid addition salts thereof.

In the descriptive portions of this invention, the following definitions apply:

The term "loweralkyl" refers to a loweralkyl hydrocarbon group containing from 1 to about 6 carbon atoms which may be straight chained or branched.

The term "loweralkoxy" signifies an alkoxy group containing from 1 to about 6 carbon atoms which may be straight chained or branched.

Compounds of this invention which are preferred are described by the general formula I
where:
R is hydrogen or loweralkyl;
$R_2$ is loweralkyl; and
$R_6$ is halo, loweralkoxy or loweralkyl.

The more preferred compounds of this invention include those compounds
where:
R is hydrogen, methyl, ethyl, propyl or butyl;
$R_2$ is methyl, ethyl, propyl, i-propyl or butyl; and
$R_6$ is chloro, bromo, fluoro, methoxy, ethoxy, methyl, ethyl, propyl, i-propyl or butyl.

The most preferred compounds are those described where:
$R_2$ is methyl or ethyl; and
$R_6$ is chloro, bromo, methoxy, methyl or ethyl.

It is well known in the pharmacological arts that non-toxic acid addition salts of pharmacologically active amine compounds do not differ in activities from their free base. The salts merely provide a convenient solubility factor.

The amines of this invention may be readily converted to their non-toxic acid addition salts by customary methods in the art. The non-toxic salts of this invention are those salts the acid component of which is pharmacologically acceptable in the intended dosages; such salts would include those prepared from inorganic acids, organic acids, higher fatty acids, high molecular weight acids, etc., and include such as: hydrochloric acid, succinic acid, hydrobromic acid, glycolic acid, sulfuric acid, lactic acid, nitric acid, salicylic acid, phosphoric acid, benzoic acid, methane sulfonic acid, nicotinic acid, benzene sulfonic acid, phthalic acid, acetic acid, stearic acid, propionic acid, oleic acid, malic acid, abietic acid, etc.

Representative compounds of this invention which are particularly useful are as follows:

1-amidino-3-(2-methyl-6-chlorophenyl)urea
1-amidino-3-(2-methyl-6-bromophenyl)urea
1-amidino-3-(2-methyl-6-fluorophenyl)urea
1-amidino-3-(2-methyl-6-methoxyphenyl)urea
1-amidino-3-(2-methyl-6-ethoxyphenyl)urea
1-amidino-3-(2,6-dimethylphenyl)urea
1-amidino-3-(2-methyl-6-ethylphenyl)urea
1-amidino-3-(2-methyl-6-propylphenyl)urea
1-amidino-3-(2-methyl-6-i-propylphenyl)urea
1-amidino-3-(2-methyl-6-butylphenyl)urea
1-amidino-3-(2-ethyl-6-chlorophenyl)urea
1-amidino-3-(2-ethyl-6-bromophenyl)urea
1-amidino-3-(2-ethyl-6-fluorophenyl)-urea
1-amidino-3-(2-ethyl-6-methoxyphenyl)urea
1-amidino-3-(2-ethyl-6-ethoxyphenyl)urea
1-amidino-3-(2-ethyl-6-methylphenyl)urea
1-amidino-3-(2,6-diethylphenyl)urea
1-amidino-3-(2-ethyl-6-propylphenyl)urea
1-amidino-3-(2-ethyl-6-i-propylphenyl)urea
1-amidino-3-(2-ethyl-6-butylphenyl)urea
1-amidino-3-(2-propyl-6-chlorophenyl)urea
1-amidino-3-(2-butyl-6-chlorophenyl)urea
1-amidino-3-(2,6-dipropylphenyl)urea
1-amidino-3-methyl-3-(2-methyl-6-chlorophenyl)urea
1-amidino-3-methyl-3-(2-methyl-6-bromophenyl)urea
1-amidino-3-methyl-3-(2-methyl-6-fluorophenyl)urea
1-amidino-3-methyl-3-(2-methyl-6-methoxyphenyl)urea
1-amidino-3-methyl-3-(2-methyl-6-ethoxyphenyl)urea
1-amidino-3-methyl-3-(2,6-dimethylphenyl)urea
1-amidino-3-methyl-3-(2-methyl-6-ethylphenyl)urea
1-amidino-3-methyl-3-(2-methyl-6-propylphenyl)urea
1-amidino-3-methyl-3-(2-methyl-6-i-propylphenyl)urea
1-amidino-3-methyl-3-(2-methyl-6-butylphenyl)urea
1-amidino-3-methyl-3-(2-ethyl-6-chlorophenyl)urea
1-amidino-3-methyl-3-(2-ethyl-6-bromophenyl)urea
1-amidino-3-methyl-3-(2-ethyl-6-fluorophenyl)urea
1-amidino-3-methyl-3-(2-ethyl-6-methoxyphenyl)urea
1-amidino-3-methyl-3-(2,6-diethylphenyl)urea
1-amidino-3-methyl-3-(2-propyl-6-chlorophenyl)urea
1-amidino-3-methyl-3-(2-i-propyl-6-chlorophenyl)urea
1-amidino-3-methyl-3-(2-butyl-6-chlorophenyl)urea
1-amidino-3-ethyl-3-(2-methyl-6-chlorophenyl)urea
1-amidino-3-ethyl-3-(2-methyl-6-bromophenyl)urea
1-amidino-3-ethyl-3-(2-methyl-6-fluorophenyl)urea
1-amidino-3-ethyl-3-(2-methyl-6-methoxyphenyl)urea
1-amidino-3-ethyl-3-(2,6-dimethylphenyl)urea
1-amidino-3-ethyl-3-(2-methyl-6-ethylphenyl)urea
1-amidino-3-ethyl-3-(2-methyl-6-propylphenyl)urea
1-amidino-3-ethyl-3-(2-methyl-6-i-propylphenyl)urea
1-amidino-3-ethyl-3-(2-methyl-6-butylphenyl)urea
1-amidino-3-propyl-3-(2-methyl-6-chlorophenyl)urea
1-amidino-3-propyl-3-(2,6-dimethylphenyl)urea The compounds of this invention may be prepared by the following general synthesis:

Condensation of a substitutedphenyl isocyanate (prepared from an aniline and phosgene in the customary manner) with guanidine results in a 1-substitutedphenyl-3-amidinourea. The reaction is carried out in a polar media using solvents such as alcohol, tetrahydrofuran, etc. It is convenient to carry out the reaction by preparing the isocyanate in the reaction media and then forming guanidine in situ by hydrolyzing guanidine carbonate with base so condensation of the isocyanate takes place when the guanidine forms and the amidinourea compound results.

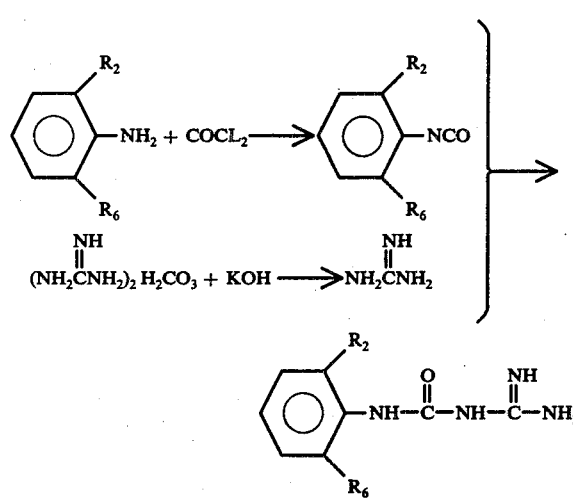

These compounds may also be prepared by degradation of the corresponding biguanide. When a 1-substitutedphenylbiguanide compound is hydrolyzed in acid at raised temperatures, then the resultant product is 1-substitutedphenyl-3-amidinourea. This reaction is preferably carried out using hydrochloric acid and the reaction time and reaction temperature will of course depend on the particular biguanide used and the concentration of the acid present. In general, the more concentrated acids will not require high temperatures or long periods of reaction time.

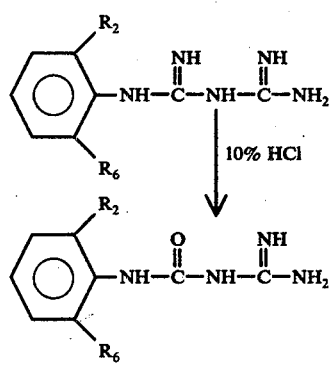

When it is desired to have R substitution the starting material of course will be an aniline having N-alkyl substitution. Reaction with phosgene results in the aniline acid chloride which is then reacted with the guanidine to prepare the amidinourea.

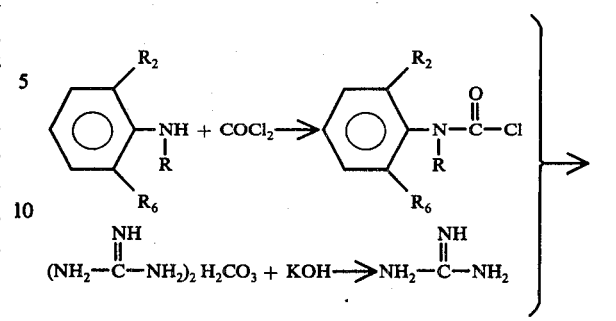

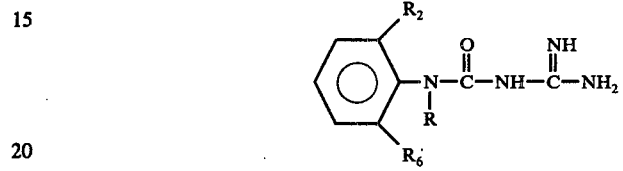

The starting anilines are either known, may be prepared by known techniques or reference to the preparation is shown. Thus, chlorination or bromination of an acetanilide or aniline may be carried out in acetic acid, or in the presence of a small amount of iodine dissolved in an inert solvent such as carbon tetrachloride. A solution of chlorine or bromine is then added while the temperature is held near 0° C. Iodination may also be carried out by known methods using iodine monochloride (ClI).

Alkylation may be carried out on an acetanilide using an alkyl halide and aluminum chloride under Friedel-Crafts conditions to obtain desired alkyl substitution.

Nitration may be carried out using fuming nitric acid at about 0° C.

A nitro compound may be hydrogenated to the corresponding amine which may then be diazotized and heated in an alcohol medium to form the alkoxy compound.

An amino compound may also be diazotized to the diazonium fluoroborate which is then thermally decomposed to the fluoro compound. Diazotization followed by a Sandmeyer type reaction may yield the bromo, chloro or iodo compound.

When an amino compound is diazotized followed by reaction with potassium ethylxanthate and then hydrolyzed, the mercapto compound results. This in turn may be alkylated to the alkylthio group which is then oxidized to the corresponding alkylsulfonyl substitutent.

A chloro, bromo or iodo compound may also be reacted with trifluoromethyliodide and copper powder at about 150° C in dimethylformamide to obtain a trifluoromethyl compound [Tetrahedron Letters:47, 4095 (1959)].

A halo compound may also be reacted with cuprous methanesulfinate in quinoline at about 150° C to obtain a methylsulfonyl compound.

Reactions may also be carried out at other stages of synthesis depending on the substituents present and the substituents desired and various combinations of the foregoing reactions will be determined by one skilled in the art in order that the desired product results. Thus, phenylamidinourea may be halogenated or nitrated as above, etc.

The biguanide starting materials are also either known, may be prepared by known procedures or may be prepared by the following general synthesis:

Condensation of cyanoguanide and an aniline in the presence of an equimolar amount of mineral acid results in the corresponding phenylbiguanide.

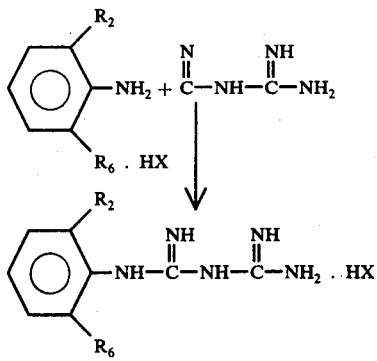

This reaction is preferably carried out on the aniline salt within a polar media or neat and using increased temperatures. The appropriately substituted product may be prepared by the reactions above when these are also carried out on the biguanide.

The compounds of this invention have a useful degree of gastric anti-secretory activity and are effective in reducing the volume and the acidity of the gastric fluid in humans and mammals. Further, these compounds produce a considerable spasmolytic action on the gastrointestinal musculature, i.e., they reduce the peristaltic action of the gastrointestinal musculature which is manifested by a delay in gastric emptying time. It should further be noted that these compounds are also characterized by their low acute oral toxicity.

In particular the amidinoureas as herein described are useful in the treatment of such gastrointestinal disorders and diseases as duodenal ulcer and peptic ulcer.

The instant compounds may be used along or in combination with other known antacids such as aluminum hydroxide, magnesium hydroxide, magnesium trisilicate, aluminum glycinate, calcium carbonate and the like.

The compounds of this invention possess blood-pressure lowering activities and are also useful as antihypertensive agents.

For all these purposes, the amidinoureas of this invention can be normally administered orally or parenterally. Orally they may be administered as tablets, aqueous or oily suspension, dispersible powders or granules, emulsions, hard or soft capsules, or syrups or elixirs. Parenterally they may be administered as a salt in solution which pH is adjusted to physiologically accepted values. Aqueous solutions are preferred.

Compositions intended for oral use may be prepared according to any method known to the art for the manufacture of pharmaceutical compositions and such compositions may contain one or more agents selected from the group consisting of sweetening agents, flavoring agents, coloring agents, preserving agents and the like, in order to provide a pharmaceutically elegant and palatable preparation.

The dosage regimen in carrying out the methods of this invention is that which insures maximum therapeutic response until improvement is obtained and thereafter the minimum effective level which gives relief. Thus, in general, the dosages are those that are therapeutically effective in the treatment of gastrointestinal disease conditions or symptoms, such as duodenal and peptic ulcer, and in the alleviation of hypertensive disorders. In general, the daily dose can be between about 0.25 mg/kg and 50 mg/kg (preferably in the range of 0.5-10 mg/kg/day), bearing in mind, of course, that in selecting the appropriate dosage in any specific case, consideration must be given to the patient's weight, general health, age, and other factors which may influence response to the drug.

Various tests in animals have been carried out to show the ability of the compounds of this invention to exhibit reactions that can be correlated with activity in humans. These tests involve such factors as the effect of the amidinoureas on gastric secretion, their spasmolytic effect, their mydriatic effect and determination of their toxicity. It has been found that the compounds of this invention when tested in the above variety of situations show a marked activity.

One such test is the gastric secretion test. This test is carried out as follows: Shay rats are fasted for 4–8 hours, and water is given ad lib. The rats are selected at random and separated into groups of 10. The animals are treated intraduodenally (I.D.) with the test compound or the vehicle immediately subsequent to the ligation of the stomach at the pyloric sphincter. The animals are sacrificed with chloroform at 4 hours post-drug administration, the stomach removed and its contents are assayed for volume, pH and total acids.

A second gastric secretion test is carried out on the dog. This is outlined in the *Handbook of Physiology, Section 6: Alimentary Canal*, Volume II: Secretion. American Physiology Society, Washington, D.C., 1967.

It has been found that the compounds of this invention when subjected to the above gastric secretion tests display marked ability to decrease gastric volume and gastric acidity. These tests are known to correlate well with gastric activity in humans and are standard tests used to determine anti-secretory properties.

To determine the anti-ulcer effectiveness the following test is employed: Male Wistar rats (130–150 grams) are fasted for 24 hours, then given reserpine at 5 mg/kg i.p. Twenty-four hours later, the stomachs are removed and examined for ulceration. Ulcers are graded on a 0–4 scale and the number of ulcers is recorded. Pretreatment with the amidinourea compounds produces a decrease in ulcer grade and the number of ulcers compared to the control reserpine-treated rats.

Determination of anti-spasmolytic properties can be carried out by the procedure as outlined by D. A. Brodie and S. K. Kundrats in their article entitled "Effect of Drugs on Gastric Emptying in Rats", *Fed. Proc.* 24:714 (1965).

Mydriasis is detected by the procedure of R. A. Turner, *Screening Methods in Pharmacology*, Academic Press, New York, and London, pp. 174–5, 1965. Acute toxicity is calculated according to the standard Litchfield-Wilcoxon procedure.

In view of the results of these tests, the pharmacological data clearly indicates that the amidinoureas of this invention can be considered to be active gastric anti-secretory and anti-spasmolytic agents which are substantially free of anti-cholinergic side effects and having a low toxicity.

Tests in animals have also been carried out to show the ability of compounds of this invention to inhibit reactions that can be correlated with hypertensive effects in humans. One such test is outlined by Jacques de Champlain, Lawrence R. Krahoff and Julius Axelrod in *Circulation Research* XXIII:479 (1968). This testing method is known to correlate well with hypertensive activity in humans and is a standard test used to determine anti-hypertensive properties. In view of the results of this test, the amidinoureas of this invention can be considered to be active anti-hypertensive agents.

The following are detailed examples which show the properties of the compounds of this invention. They are to be construed as illustrations of said compounds and not as limitations thereof.

EXAMPLE 1

1-Amidino-3-(2,6-dimethylphenyl)urea

To 12.1 g (0.1 mole) of 2,6-dimethylaniline in 300 ml of anhydrous benzene is added 325 ml of 12.5% phosgene in benzene (0.395 mole). The reaction mixture is refluxed for 2 hours and the benzene is stripped off under reduced pressure to get rid of the phosgene and the residing purified by distillation. This is 2,6-dimethylphenylisocyanate and is then dissolved in 50 ml of tetrahydrofuran and added dropwise to a heterogeneous mixture of 11.2 g of potassium hydroxide and 18 g of guanidine carbonate in 250 ml tetrahydrofuran. This mixture is stirred for 8 hours and then 35 ml of conc. hydrochloric acid is added followed by 40 ml of conc. sodium hydroxide solution maintaining the mixture cool in a cold water bath. The mixture is next poured in 1500 ml of water and the tetrahydrofuran is removed under diminished pressure. The mixture is extracted with ether which is then dried and evaporated to dryness to obtain 1-amidino-3-(2,6-dimethylphenyl)urea.

The hydrochloride solution is prepared by dissolving the free base in methanol and adding a methanolic hydrogen chloride solution to form the salt. The volume of the mixture is concentrated, ether added and 1-amidino-3-(2,6-dimethylphenyl)urea hydrochloride is filtered off.

When 2,6-dimethylaniline in the above procedure is replaced by the aniline of Table I, below, then the corresponding products of Table II, below, are prepared.

TABLE I

| | |
|---|---|
| 1 2-methyl-6-chloroaniline | 2-propyl-6-bromoaniline |
| 2 2-methyl-6-fluoroaniline | 2-propyl-6-methoxyaniline |
| 3 2-methyl-6-bromoaniline | 2-propyl-6-ethoxyaniline |
| 4 2-methyl-6-iodoaniline | 2,6-dipropylaniline |
| 5 2-methyl-6-methoxyaniline | 2-propyl-6-i-propylaniline |
| 6 2-methyl-6-ethoxyailine | 2-propyl-6-butylaniline |
| 7 2-methyl-6-ethylaniline | 2-propyl-6-trifluoromethyianiline |
| 8 2-methyl-6-propylaniline | 2-propyl-6-nitroaniline |
| 9 2-methyl-6-i-propylaniline | 2-propyl-6-methylsulfonylaniline |
| 10 2-methyl-6-butylaniline | 2-i-propyl-6-chloroaniline |
| 11 2-methyl-6-pentylaniline | 2-i-propyl-6-fluoroaniline |
| 12 2-methyl-6-hexylaniline | 2-i-propyl-6-bromoaniline |
| 13 2-methyl-6-trifluoromethylaniline | 2-i-propyl-6-methoxyaniline |
| 14 2-methyl-6-nitroaniline | 2-butyl-6-chloroaniline |
| 15 2-methyl-6-methylsulfonylaniline | 2-butyl-6-fluoroailine |
| 16 2-methyl-6-ethylsulfonylaniline | 2-butyl-6-bromoaniline |
| 17 2-ethyl-6-chloroaniline | 2-butyl-6-methoxyaniline |
| 18 2-ethyl-6-fluoroaniline | |
| 19 2-ethyl-6-bromoaniline | |
| 20 2-ethyl-6-methoxyaniline | |
| 21 2-ethyl-6-ethoxyaniline | |
| 22 2,6-diethylaniline | |
| 23 2-ethyl-6-propylaniline | |
| 24 2-ethyl-5-i-propylaniline | |
| 25 2-ethyl-6-butylaniline | |
| 26 ethyl-6-trifluoromethylaniline | |
| 27 2-ethyl-6-nitroaniline | |

TABLE I-continued

| | |
|---|---|
| 28 2-ethyl-6-methylsulfonylaniline | |
| 29 2-propyl-6-chloroaniline | |
| 30 2-propyl-6-fluoroaniline | |

TABLE II 1-amidino-3-(2-methyl-6-chlorophenyl)urea
1-amidino-3-(2-methyl-6-fluorophenyl)urea
1-amidino-3-(2-methyl-6-bromophenyl)urea
1-amidino-3-(2-methyl-6-iodophenyl)urea
1-amidino-3-(2-methyl-6-methoxyphenyl)urea
1-amidino-3-(2-methyl-6-ethoxyphenyl)urea
1-amidino-3-(2-methyl-6-ethylphenyl)urea
1-amidino-3-(2-methyl-6-propylphenyl)urea
1-amidino-3-(2-methyl-6-i-propylphenyl)urea
1-amidino-3-(2-methyl-6-butylphenyl)urea
1-amidino-3-(2-methyl-6-pentylphenyl)urea
1-amidino-3-(2-methyl-6-hexylphenyl)urea
1-amidino-3-(2-methyl-6-trifluoromethylphenyl)urea
1-amidino-3-(2-methyl-6-nitrophenyl)urea
1-amidino-3-(2-methyl-6-methylsulfonylphenyl)urea
1-amidino-3-(2-methyl-6-ethylsulfonylphenyl)urea
1-amidino-3-(2-ethyl-6-chlorophenyl)urea
1-amidino-3-(2-ethyl-6-fluorophenyl)urea
1-amidino-3-(2-ethyl-6-bromophenyl)urea
1-amidino-3-(2-ethyl-6-methoxyphenyl)urea
1-amidino-3-(2-ethyl-6-ethoxyphenyl)urea
1-amidino-3-(2,6-diethylphenyl)urea
1-amidino-3-(2-ethyl-6-propylphenyl)urea
1-amidino-3-(2-ethyl-6-i-propylphenyl)urea
1-amidino-3-(2-ethyl-6-butylphenyl)urea
1-amidino-3-(2-ethyl-6-trifluoromethylphenyl)urea
1-amidino-3-(2-ethyl-6-nitrophenyl)urea
1-amidino-3-(2-ethyl-6-methylsulfonylphenyl)urea
1-amidino-3-(2-propyl-6-chlorophenyl)urea
1-amidino-3-(2-propyl-6-fluorophenyl)urea
1-amidino-3-(2-propyl-6-bromophenyl)urea
1-amidino-3-(2-propyl-6-methoxyphenyl)urea
1-amidino-3-(2-propyl-6-ethoxyphenyl)urea
1-amidino-3-(2,6-dipropylphenyl)urea
1-amidino-3-(2-propyl-6-i-propylphenyl)urea
1-amidino-3-(2-propyl-6-butylphenyl)urea
1-amidino-3-(2-propyl-6-trifluoromethylphenyl)urea
1-amidino-3-(2-propyl-6-nitrophenyl)urea
1-amidino-3-(2-propyl-6-methylsulfonylphenyl)urea
1-amidino-3-(2-i-propyl-6-chlorophenyl)urea
1-amidino-3-(2-i-propyl-6-fluorophenyl)urea
1-amidino-3-(2-i-propyl-6-bromophenyl)urea
1-amidino-3-(2-i-propyl-6-methoxyphenyl)urea
1-amidino-3-(2-butyl-6-chlorophenyl)urea
1-amidino-3-(2-butyl-6-fluorophenyl)urea
1-amidino-3-(2-butyl-6-bromophenyl)urea
1-amidino-3-(2-butyl-6-methoxyphenyl)urea

EXAMPLE 2

1-Amidino-3-(2-chloro-6-methylphenyl)-3-methylurea

To 15.5 g (0.1 mole) of 2-chloro-6,N-dimethylaniline in 300 ml of anhydrous benzene is added 325 ml of 12.5% phosgene in benzene (0.40 mole). The reaction mixture is refluxed for 2 hours and the benzene removed under reduced pressure to also eliminate any excess phosgene. The residue is 2-chloro-6,N-dimethylaniline acid chloride. This is then dissolved in 50 ml of tetrahydrofuran and added dropwise to a heterogeneous mixture of 11.2 g of potassium hydroxide and 18 g of guanidine carbonate in 250 ml of tetrahydrofuran. The mixture is stirred for about 10 hours, acidified with conc. hydrochloric acid then bacified with conc. sodium hydroxide solution while maintaining the mixture in an acid bath. This is then poured into 1500 ml of water and the THF removed under diminished pressure. The mixture is extracted with ether, which is then dried and evaporated to dryness to obtain 1-amidino-3-(2-chloro-6-methylphenyl)-3-methylurea.

The hydrochloride salt is prepared by dissolving the free base in methanol and adding methanolic HCl to form the salt. The addition of ether accelerates the precipitation of the salt which is filtered off to obtain 1-amidino-3-(2-chloro-6-methylphenyl)-3-methylurea hydrochloride.

When 2-chloro-6,N-dimethylaniline in the above example is replaced by the anilines of Table I, below, then the corresponding products of Table II, below, are prepared.

TABLE I

2,N-dimethyl-6-fluoroaniline
2,N-dimethyl-6-bromoaniline
2,N-dimethyl-6-methoxyaniline
2,N-dimethyl-6-ethoxyaniline
2,6,N-trimethylaniline
2,N-dimethyl-6-ethylaniline
2,N-dimethyl-6-propylaniline
2,N-dimethyl-6-i-propylaniline
2,N-dimethyl-6-butylaniline
2,N-dimethyl-6-trifluoromethylaniline
2,N-dimethyl-6-nitroaniline
2,N-dimethyl-6-methylsulfonylaniline
N-methyl-2-ethyl-6-chloroaniline
N-methyl-2-ethyl-6-fluoroaniline
N-methyl-2-ethyl-6-methoxyaniline
N-methyl-2-propyl-6-chloroaniline
N-methyl-2-propyl-6-fluoroaniline
N-methyl-2-i-propyl-6-chloroaniline
N-methyl-2-i-propyl-6-fluoroaniline
N-methyl-2-butyl-6-chloroaniline
N-methyl-2-butyl-6-fluoroaniline
N-ethyl-2-methyl-6-chloroaniline
N-ethyl-2-methyl-6-fluoroaniline
N-ethyl-2-methyl-6-bromoaniline
N-ethyl-2-methyl-6-methoxyaniline
N-ethyl-2,6-dimethylaniline
N-propyl-2,6-dimethylaniline
N-propyl-2-methyl-6-fluoroaniline
N-propyl-2-methyl-6-chloroaniline

TABLE II 1-amidino-3-(2-methyl-6-fluorophenyl)-3-methylurea
1-amidino-3-(2-methyl-6-bromophenyl)-3-methylurea
1-amidino-3-(2-methyl-6-methoxyphenyl)-3-methylurea
1-amidino-3-(2-methyl-6-ethoxyphenyl)-3-methylurea
1-amidino-1-(2,6-dimethylphenyl)-1-methylurea
1-amidino-1-(2-methyl-6-ethylphenyl)-1-methylurea
1-amidino-1-(2-methyl-6-propylphenyl)-1-methylurea
1-amidino-1-(2-methyl-6-i-propylphenyl)-1-methylurea
1-aminido-1-(2-methyl-6-butylphenyl)-1-methylurea
1-amidino-1-(2-methyl-6-trifluoromethylphenyl)-1-methylurea
1-amidino-1-(2-methyl-6-nitrophenyl)-1-methylurea
1-amidino-1-(2-methyl-6-methylsulfonylphenyl)-1-methylurea
1-amidino-1-(2-ethyl-6-chlorophenyl)-1-methylurea
1-amidino-1-(2-ethyl-6-fluorophenyl)-1-methylurea
1-amidino-1-(2-ethyl-6-methoxyphenyl)-1-methylurea
1-amidino-1-(2,6-diethylphenyl)-1-methylurea
1-amidino-1-(2-propyl-6-chlorophenyl)-1-methylurea
1-amidino-1-(2-propyl-6-fluorophenyl)-1-methylurea
1-amidino-1-(2-i-propyl-6-chlorophenyl)-1-methylurea
1-amidino-1-(2-i-propyl-6-fluorophenyl)-1-methylurea
1-amidino-1-(2-butyl-6-chlorophenyl)-1-methylurea
1-amidino-1-(2-butyl-6-fluorophenyl)-1-methylurea
1-amidino-1-(2-methyl-6-fluorophenyl)-1-ethylurea
1-amidino-1-(2-methyl-6-chlorophenyl)-1-ethylurea
1-amidino-1-(2-methyl-6-bromophenyl)-1-ethylurea
1-amidino-1-(2-methyl-6-methoxyphenyl)-1-ethylurea
1-amidino-1-(2-methyl-6-ethoxyphenyl)-1-ethylurea
1-amidino-1-(2-methyl-6-propylphenyl)-1-ethylurea
1-amidino-1-(2-methyl-6-i-propylphenyl)-1-ethylurea
1-amidino-1-(2-methyl-6-butylphenyl)-1-ethylurea
1-amidino-1-(2,6-dimethylphenyl)-1-ethylurea
1-amidino-1-(2,6-dimethylphenyl)-1-propylurea
1-amidino-1-(2-methyl-6-fluorophenyl)-1-propylurea
1-amidino-1-(2-methyl-6-chlorophenyl)-1-propylurea
1-amidino-1-(2-methyl-6-ethylphenyl)-1-propylurea

EXAMPLE 3

1-Amidino-3-(2-chloro-6-methylphenyl)urea

A quantity of 20 g of 1-(2-chloro-6-methylphenyl)biguanide is added to 200 ml of 10% hydrochloric acid and the mixture is refluxed for 3 hours. The reaction mixture is then filtered hot and then chilled. The material which separates is then filtered off and recrystallized from isopropanol/water to obtain 1-amidino-3-(2-chloro-6-methylphenyl)urea hydrochloride.

The free base is prepared by dissolving the salt in 200 ml of water and adding a 10% sodium hydroxide solution until alkaline. The reaction mixture is then extracted with chloroform which is dried and evaporated to dryness to obtain 1-amidino-3-(2-chloro-6-methylphenyl)urea.

When the biguanides of Table I, below, are used in the above example in place of 1-(2-chloro-6-methylphenyl)biguanide, then the corresponding product of Table II is obtained.

TABLE I 1-(2-methyl-6-bromophenyl)biguanide
1-(2-methyl-6-chlorophenyl)biguanide
1-(2-methyl-6-fluorophenyl)biguanide
1-(2-methyl-6-methoxyphenyl)biguanide
1-(2-methyl-6-ethoxyphenyl)biguanide
1-(2,6-dimethylphenyl)biguanide
1-(2-methyl-6-ethylphenyl)biguanide
1-(2-methyl-6-propylphenyl)biguanide
1-(2-methyl-6-i-propylphenyl)biguanide
1-(2-methyl-6-butylphenyl)biguanide
1-(2-ethyl-6-chlorophenyl)biguanide
1-(2-ethyl-6-bromophenyl)biguanide
1-(2-ethyl-6-fluorophenyl)biguanide
1-(2-ethyl-6-methoxyphenyl)biguanide
1-(2-ethyl-6-ethoxyphenyl)biguanide
1-(2,6-diethylphenyl)biguanide
1-(2-ethyl-6-propylphenyl)biguanide
1-(2-ethyl-6-i-propylphenyl)biguanide
1-(2-ethyl-6-butylphenyl)biguanide
1-(2-propyl-6-chlorophenyl)biguanide
1-(2-i-propyl-6-chlorophenyl)biguanide
1-(2-butyl-6-chlorophenyl)biguanide
1-(2,6-dipropylphenyl)biguanide
1-methyl-1-(2-methyl-6-chlorophenyl)biguanide 1-methyl-1-(2-methyl-6-bromophenyl)biguanide
1-methyl-1-(2-methyl-6-fluorophenyl)biguanide
1-methyl-1-(2-methyl-6-methoxyphenyl)biguanide
1-methyl-1-(2-methyl-6-ethoxyphenyl)biguanide
1-methyl-1-(2,6-dimethylphenyl)biguanide
1-methyl-1-(2-methyl-6-ethylphenyl)biguanide
1-methyl-1-(2-methyl-6-propylphenyl)biguanide
1-methyl-1-(2-methyl-6-i-propylphenyl)biguanide
1-methyl-1-(2-methyl-6-butylphenyl)biguanide
1-methyl-1-(2-ethyl-6-chlorophenyl)biguanide
1-methyl-1-(2-ethyl-6-bromophenyl)biguanide
1-methyl-1-(2-ethyl-6-fluorophenyl)biguanide
1-methyl-1-(2-ethyl-6-methoxyphenyl)biguanide
1-methyl-1-(2,6-diethylphenyl)biguanide
1-methyl-1-(2-propyl-6-chlorphenyl)biguanide
1-methyl-1-(2-i-propyl-6-chlorphenyl)biguanide
1-methyl-1-(2-butyl-6-chlorophenyl)biguanide
1-ethyl-1-(2-methyl-6-chlorophenyl)biguanide
1-ethyl-1-(2-methyl-6-bromophenyl)biguanide
1-ethyl-1-(2-methyl-6-fluorophenyl)biguanide
1-ethyl-1-(2-methyl-6-methoxyphenyl)biguanide
1-ethyl-1-(2,6-dimethylphenyl)biguanide
1-ethyl-1-(2-methyl-6-ethylphenyl)biguanide
1-ethyl-1-(2-methyl-6-propylphenyl)biguanide
1-ethyl-1-(2-methyl-6-i-propylphenyl)biguanide
1-ethyl-1-(2-methyl-6-butylphenyl)biguanide
1-propyl-1-(2,6-dimethylphenyl)biguanide
1-butyl-1-(2,6-dimethylphenyl)biguanide
1-propyl-1-(2,6-diethylphenyl)biguanide
1-butyl-1-(2,6-diethylphenyl)biguanide

TABLE II 1-amidino-3-(2-methyl-6-chlorophenyl)urea
1-amidino-3-(2-methyl-6-bromophenyl)urea
1-amidino-3-(2-methyl-6-fluorophenyl)urea
1-amidino-3-(2-methyl-6-methoxyphenyl)urea
1-amidino-3-(2-methyl-6-ethoxyphenyl)urea
1-amidino-3-(2,6-dimethylphenyl)urea
1-amidino-3-(2-methyl-6-ethylphenyl)urea
1-amidino-3-(2-methyl-6-propylphenyl)urea
1-amidino-3-(2-methyl-6-i-propylphenyl)urea
1-amidino-3-(2-methyl-6-butylphenyl)urea
1-amidino-3-(2-ethyl-6-chlorophenyl)urea
1-amidino-3-(2-ethyl-6-bromophenyl)urea
1-amidino-3-(2-ethyl-6-fluorophenyl)urea
1-amidino- 3-(2-ethyl-6-methoxyphenyl)urea
1-amidino-3-(2-ethyl-6-ethoxyphenyl)urea
1-amidino-3-(2-ethyl-6-methylphenyl)urea
1-amidino-3-(2,6-diethylphenyl)urea
1-amidino-3-(2-ethyl-6-propylphenyl)urea
1-amidino-3-(2-ethyl-6-i-propylphenyl)urea
1-amidino-3-(2-ethyl-6-butylphenyl)urea
1-amidino-3-(2-propyl-6-chlorophenyl)urea
1-amidino-3-(2-butyl-6-clorophenyl)urea
1-amidino-3-(2,6-dipropylphenyl)urea
1-amidino-3-methyl-3-(2-methyl-6-chlorophenyl)urea
1-amidino-3-methyl-3-(2-methyl-6-bromophenyl)urea
1-amidino-3-methyl-3-(2-methyl-6-fluorophenyl)urea
1-amidino-3-methyl-3-(2-methyl-6-methoxyphenyl)urea
1-amidino-3-methyl-3-(2-methyl-6-ethoxyphenyl)urea
1-amidino-3-methyl-3-(2,6-dimethylphenyl)urea
1-amidino-3-methyl-3-(2-methyl-6-ethylphenyl)urea
1-amidino-3-methyl-3-(2-methyl-6-propylphenyl)urea
1-amidino-3-methyl-3-(2-methyl-6-i-propylphenyl)urea
1-amidino-3-methyl-3-(2-methyl-6-butylphenyl)urea
1-amidino-3-methyl-3-(2-ethyl-6-chlorophenyl)urea
1-amidino-3-methyl-3-(2-ethyl-6-bromophenyl)urea
1-amidino-3-methyl-3-(2-ethyl-6-fluorophenyl)urea
1-amidino-3-methyl-3-(2-ethyl-6-methoxyphenyl)urea
1-amidino-3-methyl-3-(2,6-diethylphenyl)urea
1-amidino-3-methyl-3-(2-propyl-6-chlorophenyl)urea
1-amidino-3-methyl-3-(2-i-propyl-6-chlorophenyl)urea
1-amidino-3-methyl-3-(2-butyl-6-chlorophenyl)urea
1-amidino-3-ethyl-3-(2-methyl-6-chlorophenyl)urea
1-amidino-3-ethyl-3-(2-methyl-6-bromophenyl)urea
1-amidino-3-ethyl-3-(2-methyl-6-fluorophenyl)urea
1-amidino-3-ethyl-3-(2-methyl-6-methoxyphenyl)urea
1-amidino-3-ethyl-3-(2,6-dimethylphenyl)urea
1-amidino-3-ethyl-3-(2-methyl-6-ethylphenyl)urea
1-amidino-3-ethyl-3-(2-methyl-6-propylphenyl)urea
1-amidino-3-ethyl-3-(2-methyl-i-propylphenyl)urea
1-amidino-3-ethyl-3-(2-methyl-6-butylphenyl)urea
1-amidino-3-propyl-3-(2-methyl-6-chlorophenyl)urea
1-amidino-3-propyl-3-(2,6-dimethylphenyl)urea
1-amidino-3-propyl-3-(2,6-dimethylphenyl)urea
1-amidino-3-butyl-3-(2,6-dimethylphenyl)urea
1-amidino-3-propyl-3-(2,6-diethylphenyl)urea
1-amidino-3-butyl-3-(2,6-diethylphenyl)urea

We claim:
1. A compound of formula

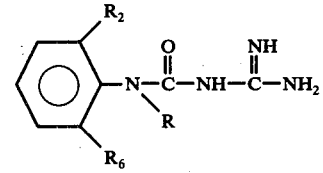

where:
R is hydrogen or loweralkyl;
$R_2$ is loweralkyl;
$R_6$ is halo, loweralkoxy, loweralkyl, haloloweralkyl, nitro or loweralkylsulfonyl; and the non-toxic acid addition salts thereof.

2. A compound according to claim 1
where:
R is hydrogen or loweralkyl;
$R_2$ is loweralkyl; and
$R_6$ is halo, loweralkoxy or loweralkyl.

3. A compound according to claim 2
where:
R is hydrogen, methyl or ethyl;
$R_2$ is methyl, ethyl, propyl, i-propyl or butyl; and
$R_6$ is chloro, bromo, fluoro, methoxy, ethoxy, methyl, ethyl, propyl, i-propyl or butyl.

4. A compound according to claim 3
where:
R is hydrogen or methyl;
$R_2$ is methyl or ethyl; and
$R_6$ is chloro, bromo, methoxy, methyl or ethyl.

5. A compound according to claim 4 where R is hydrogen.

6. A compound according to claim 4 where R is methyl.

7. A compound according to claim 5 where $R_2$ is methyl.

8. A compound according to claim 7 where $R_6$ is chloro thus forming 1-amidino-3-(2-methyl-6-chlorophenyl)urea.

9. A compound according to claim 7 where $R_6$ is bromo thus forming 1-amidino-3-(2-methyl-6-bromophenyl)urea.

10. A compound according to claim 7 where $R_6$ is methoxy thus forming 1-amidino-3-(2-methyl-6-methoxyphenyl)urea.

11. A compound according to claim 7 where $R_6$ is methyl thus forming 1-amidino-3-(2,6-dimethylphenyl)urea.

12. A compound according to claim 7 where $R_6$ is ethyl thus forming 1-amidino-3-(2-methyl-6-ethylphenyl)urea.

13. A compound according to claim 5 where $R_2$ is ethyl.

14. A compound according to claim 13 where $R_6$ is chloro thus forming 1-amidino-3-(2-ethyl-6-chlorophenyl)urea.

15. A compound according to claim 13 where $R_6$ is bromo thus forming 1-amidino-3-(2-ethyl-6-bromophenyl)urea.

16. A compound according to claim 13 where $R_6$ is methoxy thus forming 1-amidino-3-(2-ethyl-6-methoxyphenyl)urea.

17. A compound according to claim 13 where $R_6$ is ethyl thus forming 1-amidino-3-(2,6-diethylphenyl)urea.

18. A compound according to claim 6 where $R_2$ is methyl.

19. A compound according to claim 18 where $R_6$ is chloro thus forming 1-amidino-3-methyl-3-(2-methyl-6-chlorophenyl)urea.

20. A compound according to claim 18 where $R_6$ is bromo thus forming 1-amidino-3-methyl-3-(2-methyl-6-bromophenyl)urea.

21. A compound according to claim 8 where $R_6$ is methoxy thus forming 1-amidino-3-methyl-3-(2-methyl-6-methoxyphenyl)urea.

22. A compound according to claim 18 where $R_6$ is methyl thus forming 1-amidino-3-methyl-3-(2,6-dimethylphenyl)urea.

23. A compound according to claim 18 where $R_6$ is ethyl thus forming 1-amidino-3-methyl-3-(2-methyl-6-ethylphenyl)urea.

24. A compound according to claim 6 where $R_2$ is ethyl.

25. A compound according to claim 24 where $R_6$ is chloro thus forming 1-amidino-3-methyl-3-(2-ethyl-6-chlorophenyl)urea.

26. A compound according to claim 24 where $R_6$ is bromo thus forming 1-amidino-3-methyl-3-(2-ethyl-6-bromopheny)urea.

27. A compound according to claim 24 where $R_6$ is methoxy thus forming 1-amidino-3-methyl-3-(2-ethyl-6-methoxyphenyl)urea.

28. A compound according to claim 24 where $R_6$ is ethyl thus forming 1-amidino-3-methyl-3-(2,6-diethylphenyl)urea.

29. A compound according to claim 2 where $R_2$ and $R_6$ are methyl.

30. A compound according to claim 2 where $R_2$ and $R_6$ are ethyl.

31. A method for treating gastrointestinal spasms comprising administering to a patient suffering from said gastrointestinal spasms a therapeutically effective amount between 0.25 mg/kg and 50 mg/kg per day of at least one compound of the formula:

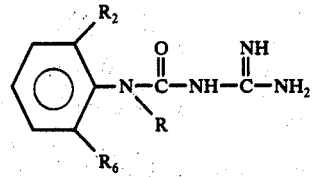

where:
R is hydrogen or loweralkyl;
$R_2$ is loweralkyl;
$R_6$ is halo, loweralkoxy, loweralkyl, haloloweralkyl, nitro or loweralkylsulfonyl; and the non-toxic acid addition salts thereof.

32. A method according to claim 31 where:
R is hydrogen or loweralkyl;
$R_2$ is loweralkyl; and
$R_6$ is halo, loweralkoxy or loweralkyl.

33. A method according to claim 32 where:
R is hydrogen, methyl, ethyl, propyl or butyl;
$R_2$ is methyl, ethyl, propyl, i-propyl or butyl; and
$R_6$ is chloro, bromo, fluoro, methoxy, ethoxy, methyl, ethyl, propyl, i-propyl or butyl.

34. A method according to claim 33 where:
$R_2$ is methyl ethyl; and
$R_6$ is chloro, bromo, methoxy, methyl or ethyl.

35. The method according to claim 34 where R is hydrogen.

36. The method according to claim 34 where R is methyl.

37. The method according to claim 35 where $R_2$ is methyl.

38. The method according to claim 37 where $R_6$ is chloro thus forming 1-amidino-3-(2-methyl-6-chlorophenyl)urea.

39. The method according to claim 37 where $R_6$ is bromo thus forming 1-amidino-3-(2-methyl-6-bromophenyl)urea.

40. The method according to claim 37 where $R_6$ is methoxy thus forming 1-amidino-3-(2-methyl-6-methylphenyl)urea.

41. The method according to claim 37 where $R_6$ is methyl thus forming 1-amidino-3-(2,6-dimethylphenyl)urea.

42. The method according to claim 37 where $R_6$ is ethyl thus forming 1-amidino-3-(2-methyl-6-ethylphenyl)urea.

43. The method according to claim 35 where $R_2$ is ethyl.

44. The method according to claim 43 where $R_6$ is chloro thus forming 1-amidino-3-(2-ethyl-6-chlorophenyl)urea.

45. The method according to claim 43 where $R_6$ is bromo thus forming 1-amidino-3-(2-ethyl-6-bromophenyl)urea.

46. The method according to claim 43 where $R_6$ is methoxy thus forming 1-amidino-3-(2-ethyl-6-methoxyphenyl)urea.

47. The method according to claim 43 where $R_6$ is ethyl thus forming 1-amidino-3-(2,6-diethylphenyl)urea.

48. The method according to claim 36 where $R_2$ is methyl.

49. The method according to claim 48 where $R_6$ is chloro thus forming 1-amidino-3-methyl-3-(2-methyl-6-chlorophenyl)urea.

50. The method according to claim 48 where $R_6$ is bromo thus forming 1-amidino-3-methyl-3-(2-methyl-6-bromophenyl)urea.

51. The method according to claim 48 where $R_6$ is methoxy thus forming 1-amidino-3-methyl-3-(2-methyl-6-methoxyphenyl)urea.

52. The method according to claim 48 where $R_6$ is methyl thus forming 1-amidino-3-methyl-3-(2,6-dimethylphenyl)urea.

53. The method according to claim 48 where $R_6$ is ethyl thus forming 1-amidino-3-methyl-3-(2-methyl-6-ethylphenyl)urea.

54. The method according to claim 36 where $R_2$ ethyl.

55. The method according to claim 54 where $R_6$ is chloro thus forming 1-amidino-3-methyl-3-(2-ethyl-6-chlorophenyl)urea.

56. The method according to claim 54 where $R_6$ is bromo thus forming 1-amidino-3-methyl-3-(2-ethyl-6-bromophenyl)urea.

57. The method according to claim 54 where $R_6$ is methoxy thus forming 1-amidino-3-methyl-3-(2-ethyl-6-methoxyphenyl)urea.

58. The method according to claim 54 where $R_6$ is ethyl thus forming 1-amidino-3-methyl-3-(2,6-diethylphenyl)urea.

* * * * *